United States Patent
Zhang et al.

(10) Patent No.: US 9,884,870 B2
(45) Date of Patent: Feb. 6, 2018

(54) POLYMORPHIC SUBSTANCE OF YONKENAFIL HYDROCHLORIDE, PREPARATION METHOD THEREFOR, AND COMPOSITION AND USE THEREOF

(71) Applicant: Yangtze River Pharmaceutical Group Co., Ltd., Jiangsu (CN)

(72) Inventors: Haibo Zhang, Jiangsu (CN); Lingwu Chen, Jiangsu (CN); Xianfeng Lu, Jiangsu (CN); Huixing Liang, Jiangsu (CN); Yongfeng Wang, Jiangsu (CN); Lianyong Shi, Jiangsu (CN); Hongpeng Luo, Jiangsu (CN)

(73) Assignee: Yangtze River Pharmaceutical Group Co., Ltd., Taizhou, Jiangsu (CN)

( * ) Notice: Subject to any disclaimer, the term of this patent is extended or adjusted under 35 U.S.C. 154(b) by 0 days.

(21) Appl. No.: 15/535,502

(22) PCT Filed: Nov. 19, 2015

(86) PCT No.: PCT/CN2015/095059
§ 371 (c)(1),
(2) Date: Jun. 13, 2017

(87) PCT Pub. No.: WO2016/095650
PCT Pub. Date: Jun. 23, 2016

(65) Prior Publication Data
US 2017/0349592 A1    Dec. 7, 2017

(30) Foreign Application Priority Data

Dec. 19, 2014 (CN) .......................... 2014 1 0799600

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
None
See application file for complete search history.

(56) References Cited

FOREIGN PATENT DOCUMENTS

| CN | 1552714 A | 12/2004 |
|---|---|---|
| CN | 104530054 A | 4/2015 |

OTHER PUBLICATIONS

International Search Report of PCT/CN2015/095059, dated Jan. 20, 2016.

*Primary Examiner* — Alicia L Otton
(74) *Attorney, Agent, or Firm* — Banner & Witcoff, Ltd.

(57) ABSTRACT

The present application discloses an A-type polymorphic substance of yonkenafil hydrochloride and a preparation method, a composition and use thereof. The powder diffraction pattern of the A-type polymorphic substance of yonkenafil hydrochloride comprises diffraction peaks at three or more 2θ values selected from: 8.4±0.2°, 11.3±0.2°, 13.9±0.2°, 14.2±0.2°, 14.7±0.2°, 16.8±0.2°, 17.1±0.2°, 19.7±0.2°, 21.0±0.2°, 21.7±0.2°, 22.4±0.2°, 23.3±0.2°, 23.8±0.2°, 26.8±0.2°, 27.5±0.2°, 28.0±0.2°.

75 Claims, 2 Drawing Sheets

POLYMORPHIC SUBSTANCE OF YONKENAFIL HYDROCHLORIDE, PREPARATION METHOD THEREFOR, AND COMPOSITION AND USE THEREOF

TECHNICAL FIELD

The present application relates to, but is not limited to, the field of a pharmaceutical technology, and specifically relates to, but is not limited to, a polymorphic substance of phosphodiesterase 5 inhibitor yonkenafil hydrochloride, and preparation methods, compositions and uses thereof.

BACKGROUND OF THE RELATED ART

Erectile dysfunction, ED, refers to the persistent inability to achieve and/or maintain a full erection to obtain a satisfactory sexual life. According to the different causes, ED can be divided into three categories of the psychogenic, organic and mixed, which is closely related to age but not an inevitable disease during the aging process. Primary risk factors of ED include: hypertension, hyperlipidemia, diabetes, coronary and peripheral vascular disease, pelvic organ or spinal cord injury or surgery. According to statistics, currently about 150 million males worldwide suffer from different extents of ED, and by 2025, the number of the patients with ED will be doubled. There are many therapeutic regimens available for ED, such as oral administration of drug phosphodiesterase 5 (PDE5) inhibitors, dopaminergic activators, and a receptor blockers, intracavernous injection therapy, vacuum negative pressure device treatment, penile prosthesis treatment, etc. Among them, the selective phosphodiesterase 5 (PDE5) inhibitor is found to be the most mature ED therapeutic drugs in research, and also is the first-line drug for the clinical treatment of ED. Currently, five types of such drugs that have been approved for the sale are Sildenafil, Tadalafil, Vardenafil, Udenafil and Mirodenafil.

Chinese patent application No. CN03142399.X, published in 2004, discloses a series of compounds having a pyrrolopyrimidone structure and their use in the preparation of a medicament for the treatment of animal sexual dysfunction including human sexual dysfunction, in particular male penile erectile dysfunction and diseases associated with PDE5 function; wherein, compound 1-HCl, i.e., 2-[2-ethoxy-5-(4-ethyl piperazine-1-sulfonyl)phenyl]-5-methyl-7-n-propyl-3,7-dihydropyrrolo[2,3-d]pyrimidin-4-one monohydrochloride has been named as yonkenafil hydrochloride in public as a characteristic compound of Example 1 in the Chinese Patent Application No. CN03142399.X. This patent application only describes the preparation method for this compound in detail, but does not relate to the study of the crystalline form of the compound.

Content of the Invention

The form of the pharmaceutical compound is of importance, and it relates to the study of suitable dosage forms, since if the form of the compound cannot be kept constant in the clinical and stability studies, the exact dose in the application and the assay cannot be compared between one batch and another batch. Once the pharmaceutical compound is used as a product, it is important to understand the crystalline form of the compound used in each dosage form in order to ensure that the same form of the drug is used in the production process and the same dosage of the drug is contained in each dosage form. Solid material in the nature may be in three states of a stable state, a metastable state, and an unstable state, and so does the crystal material. The state of the different crystalline forms of the compound will be converted with environmental condition changes (such as temperature, humidity, light and pressure, etc.), and since the stability of pharmaceutical crystalline form substances will affect the clinical efficacy and safety of drugs, the stability study on the state of the crystalline form substances is needed. Stable or metastable (conditionally stable) crystalline form substances have druggability, but unstable crystalline form substances have no druggability, so it is very necessary to use the state of pharmaceutical crystalline form substances with stable advantages as drug raw material and the formulation crystalline form thereof to ensure the clinical effectiveness, safety and quality control of the drug.

The following is a summary of the subject matters that are described in detail herein. This summary is not intended to limit the protection scope of the claims.

An embodiment of the present invention provides a stable, A-type polymorphic substance of yonkenafil hydrochloride.

An embodiment of the present invention also provides a preparation method for the stable, A-type polymorphic substance of yonkenafil hydrochloride as described by any one of the embodiments of the present invention.

An embodiment of the present invention also provides an A-type polymorphic substance of yonkenafil hydrochloride prepared by the preparation method for the stable, A-type polymorphic substance of yonkenafil hydrochloride as described by any one of the embodiments of the present invention.

An embodiment of the present invention also provides a pharmaceutical composition comprising the stable, A-type polymorphic substance of yonkenafil hydrochloride as described by any one of the embodiments of the present invention.

An embodiment of the present invention also provides use of the stable, A-type polymorphic substance of yonkenafil hydrochloride as described by any one of the embodiments of the present invention.

In particular, the present invention provides an A-type polymorphic substance of yonkenafil hydrochloride, and the X-ray powder diffraction pattern of the polymorphic substance comprises diffraction peaks at three or more 2θ values selected from 8.4°±0.2°, 11.3°±0.2° 13.9°±0.2° 14.2°±0.2° 14.7°±0.2° 16.8°±0.2° 17.1°±0.2° 19.7°±0.2°, 21.0°±0.2° 21.7°±0.2° 22.4°±0.2° 23.3°±0.2° 23.8°±0.2° 26.8°±0.2° 27.5°±0.2°, 28.0°±0.2°.

In an embodiment of the present invention, the X-ray powder diffraction pattern of the A-type polymorphic substance of yonkenafil hydrochloride may comprise 8.4°±0.2°, 11.3°±0.2° 13.9°±0.2° 14.2°±0.2° 14.7°±0.2° 16.8°±0.2° 17.1°±0.2° 19.7°±0.2° 21.0°±0.2° 21.7°±0.2° 22.4°±0.2° 23.3°±0.2° 23.8°±0.2° 26.8°±0.2° 27.5°±0.2° 28.0°±0.2°.

In one embodiment of the present invention, the X-ray powder diffraction pattern of the A-type polymorphic substance of yonkenafil hydrochloride may be substantially consistent with that shown in FIG. 1.

In an embodiment of the present invention, the analysis pattern of the differential scanning calorimetry of the A-type polymorphic substance of yonkenafil hydrochloride may have endothermic peaks at 34-133° C. and 231-250° C., respectively.

In one embodiment of the present invention, the analysis pattern of the differential scanning calorimetry of the A-type polymorphic substance of yonkenafil hydrochloride may have endothermic peaks at 86.4° C. and 237.9° C., respectively.

In one embodiment of the present invention, the analysis pattern of the differential scanning calorimetry of the A-type polymorphic substance of yonkenafil hydrochloride may be substantially consistent with that shown in FIG. 2.

In an embodiment of the present invention, the A-type polymorphic substance of yonkenafil hydrochloride, provided by embodiments of the present invention, may have cell parameters substantially as follows:

cell dimension: a (Å) is equal to 19.1±0.1
b (Å) is equal to 12.7±0.1
c (Å) is equal to 11.3±0.1
volume is equal to 2741±30 Å$^3$
space group is P2$_1$/c
density (calculated value) (g/cm$^3$) is 1.31±0.01.

In another aspect, an embodiment of the present invention provides a preparation method for an A-type polymorphic substance of yonkenafil hydrochloride, comprising:

suspending yonkenafil hydrochloride in an aqueous solution or an organic solvent/water solution, heating to dissolve the yonkenafil hydrochloride, slowly cooling and crystallizing, filtering to collect solid, and drying, to obtain the A-type polymorphic substance of yonkenafil hydrochloride;

or, achieving an equilibrium of yonkenafil hydrochloride in an aqueous solution or an organic solvent/water solution, filtering and drying to obtain the A-type polymorphic substance of yonkenafil hydrochloride;

wherein the organic solvent is a solvent capable of dissolving yonkenafil hydrochloride and miscible with water under the heating conditions.

In an embodiment of the present invention, said yonkenafil hydrochloride suspended in an organic solvent/water solution may be prepared by using Chinese Patent CN03142399.X.

In an embodiment of the present invention, said organic solvent may be selected from one or more of ethanol, methanol, n-propanol, acetonitrile, isopropanol, acetone, dimethylsulfoxide, N-methylpyrrolidone, or tetrahydrofuran.

In an embodiment of the present invention, the volume ratio of the organic solvent to water may be 99/1-0/100.

In an embodiment of the present invention, the volume ratio of the organic solvent to water may be 98/2-40/60.

In an embodiment of the present invention, said heating temperature may be in the range of 40° C.~100° C.

In an embodiment of the present invention, said heating temperature may be in the range of 60° C.~90° C.

In an embodiment of the present invention, the rate of said slowly cooling may be in the range of 0.1° C./min~2.0° C./min.

In an embodiment of the present invention, the rate of said slowly cooling may be in the range of 0.1° C./min~0.8° C./min.

In an embodiment of the present invention, said yonkenafil hydrochloride refers to monohydrochloride of yonkenafil.

In a third aspect, an embodiment of the present invention provides an A-type polymorphic substance of yonkenafil hydrochloride prepared by the preparation method for the A-type polymorphic substance of yonkenafil hydrochloride as described by any one of the embodiments of the present invention.

In a fourth aspect, the present invention provides a pharmaceutical composition comprising an A-type polymorphic substance of yonkenafil hydrochloride as described by any one of the embodiments of the present invention.

In an embodiment of the present invention, this pharmaceutical composition may be formulated as a solid oral formulation such as a tablet, a pill, a capsule and a powder; and also as a liquid oral formulation such as a suspension, a solution, an emulsion and a syrup.

In an embodiment of the present invention, this pharmaceutical composition may contain conventional various excipients such as a wetting agent, a sweetener, a fragrance and a preservative, and may also contain conventional functional excipients such as a filler (starch, saccharides), an adhesive (carboxymethylcellulose, etc.), a dispersant (sodium carbonate, calcium carbonate, etc.), a diluent (glycerol), an absorption enhancer (quaternary ammonium compounds), a lubricant (stearates) and an absorbent (kaolin); may also be formulated into a paste for external use; and may also be suitable to be formulated into an intravenous injection.

In general, for human, the oral administration of the pharmaceutical composition of the A-type polymorphic substance of yonkenafil hydrochloride of the embodiments of the present invention is a preferred route, since this route is the most convenient route, and avoids the inconvenience encountered when intracavernous administration is performed. A parenteral administration, such as sublingual, buccal, transdermal and injectable administration, may be used when the patient suffers from a dysphagia, or from a drug absorption injury after oral administration.

In a fifth aspect, an embodiment of the present invention provides use of the A-type polymorphic substance of yonkenafil hydrochloride of any one of the embodiments of the present invention, or the A-type polymorphic substance of yonkenafil hydrochloride prepared by the preparation method for the A-type polymorphic substance of yonkenafil hydrochloride of any one of the embodiments of the present invention, or the pharmaceutical composition comprising the A-type polymorphic substance of yonkenafil hydrochloride of any one of the embodiments of the present invention, in the preparation of a medicament for treating or preventing male animal erectile dysfunction including human erectile dysfunction, and diseases associated with phosphodiesterase 5.

In an embodiment of the present invention, said diseases associated with phosphodiesterase 5 may be male sexual dysfunction (erectile dysfunction), female sexual dysfunction, premature labor, dysmenorrhea, benign prostatic hyperplasia, bladder obstruction, incontinence, regular or irregular angina, hypertension, pulmonary hypertension, congestive heart failure, arteriosclerosis, stroke, peripheral circulatory system diseases, openness reduction of blood vessels, chronic asthma, allergic asthma, bronchitis, allergic rhinitis, glaucoma, gastrointestinal disorders, convulsion precursors, Kawasaki syndrome, nitrate tolerance, multiple sclerosis, diabetic peripheral neurological syndrome, Alzheimer's disease, acute respiratory failure, psoriasis, skin gangrene, cancer cell metastasis, hair loss, nutcracker esophagus, anal fissure and hypoxic vasoconstriction.

The A-type polymorphic substance of yonkenafil hydrochloride provided in the embodiments of the present invention has excellent physical and chemical stability and is easy to be industrially produced as a pharmaceutically acceptable, stable, novel crystalline form of yonkenafil hydrochloride.

Upon reading and understanding the drawings and detailed description, other aspects can be understood.

BRIEF DESCRIPTION OF DRAWINGS

The accompanying drawings are provided to further understand the embodiments of the present invention and constitute a part of the description, and are used together with the following preferred embodiments of the present invention to explain the examples of the present invention without limiting the examples of the present invention. In the drawings.

PREFERRED EMBODIMENTS OF THE PRESENT INVENTION

Figure 1:
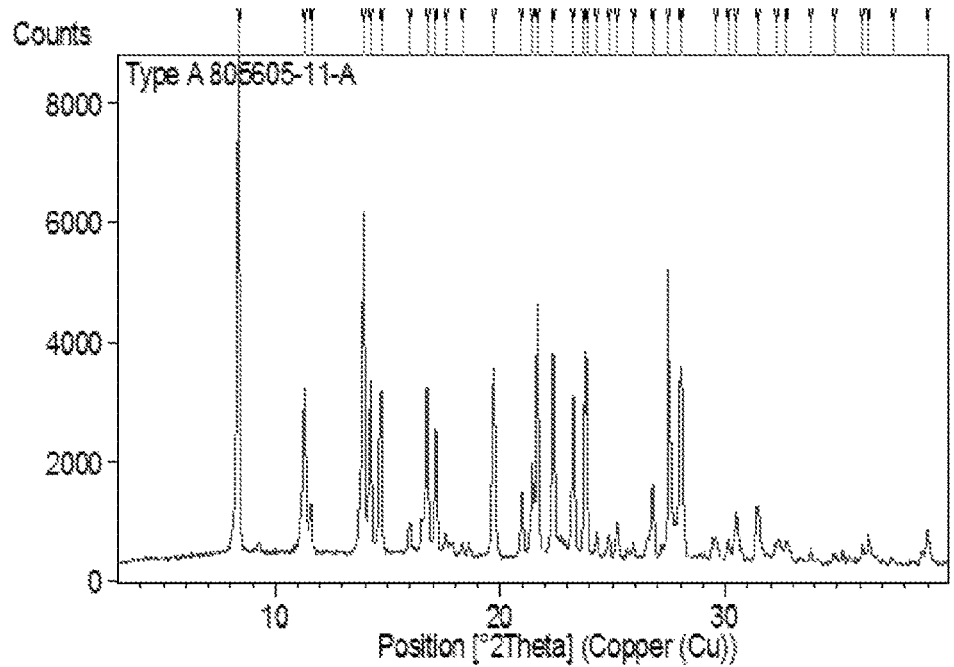
FIG. 1 is an X-RD pattern of the A-type polymorphic substance of yonkenafil hydrochloride.

The present invention will be further described in detail below in conjunction with the examples, and it should be understood that the preferred embodiments described herein are for the purpose of illustration and explanation only and are not used to limit the present invention.

The XRPD pattern of the embodiments of the present invention is acquired on a PANalytical Empyrean X-ray powder diffraction analyzer with the following XRPD parameters:

| Parameter | Reflection parameters |
|---|---|
| X-ray | Cu, kα, Kα1 (Å): 1.540598; Kα2 (Å): 1.544426 Kα2/Kα1 Strength ratio: 0.50 |
| X-ray light tube setting | 45 kV, 40 mA |
| Divergence slit | automatic |
| Monochromator | none |
| Scan mode | continuous |
| Scan range (°2Theta) | 3°~40° |
| Scan step size (°2Theta) | 0.013 |
| Scan time (min) | about 4 |

The DSC pattern of the embodiments of the present invention is acquired on a TA Q200/Q2000 differential scanning calorimeter. The experimental parameters are as follows:

| Parameter | Setting |
|---|---|
| Sample plate | Aluminum plate, gland |
| Temperature range/° C. | Room temperature * to setting temperature |
| Heating rate/° C./min | 10 |
| Protective gas | Nitrogen gas |

*: Room temperature is generally 25 ± 3° C.

Example 1

The B-type polymorphic substance of yonkenafil hydrochloride (1.0 g, the preparation method thereof was seen in the comparative example) and 95 volume % of an ethanol aqueous solution (6 mL) were added to a flask at the condition of room temperature and stirred for 2 h, separated by filtration, and the resulting solid was dried under reduced pressure, to give the A-type polymorphic substance of yonkenafil hydrochloride (0.8 g). Its X-RD diffraction pattern was shown in FIG. 1, and DSC was shown in FIG. 2.

Example 2

The B-type polymorphic substance of yonkenafil hydrochloride (10 g) and 50 volume % of a methanol aqueous solution (3 mL) were added to a flask at the condition of room temperature, heated to 70° C. to be dissolved, slowly cooled to −10° C., filtered, and the resulting solid was dried under reduced pressure, to give the A-type polymorphic substance of yonkenafil hydrochloride (0.8 g). Its X-RD diffraction pattern was shown in FIG. 1, and DSC was shown in FIG. 2.

Example 3

Figure 2:
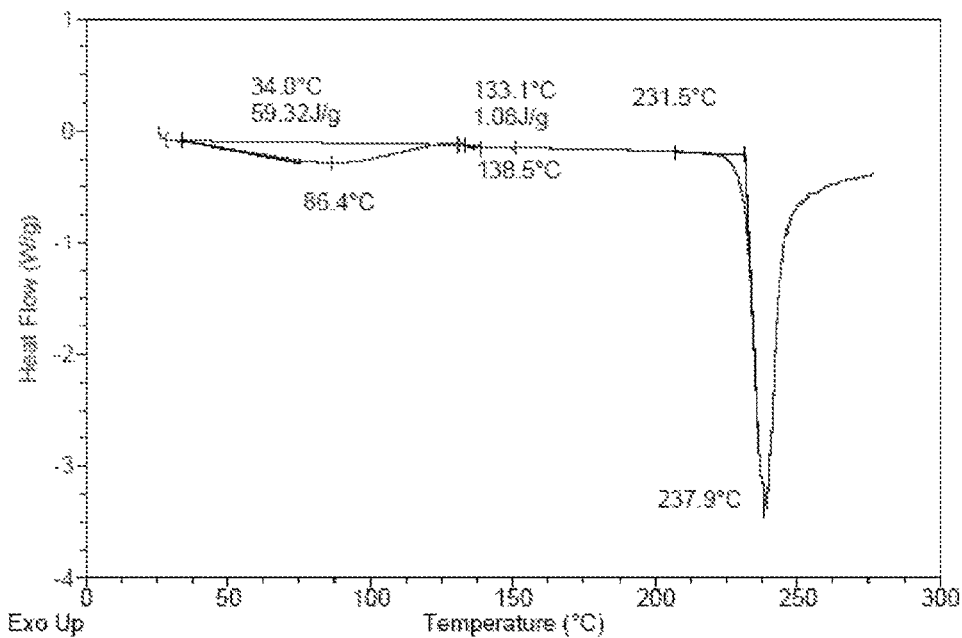
FIG. 2 is a DSC pattern of the A-type polymorphic substance of yonkenafil hydrochloride.

The A-type polymorphic substance of yonkenafil hydrochloride (0.5 g), and the B-type polymorphic substance (0.5 g) and water (2 mL) were added to a flask at the condition of room temperature, heated to 70° C. to be dissolved, slowly cooled to −5° C., filtered, and the resulting solid was dried under reduced pressure, to give the A-type polymorphic substance of yonkenafil hydrochloride (0.7 g). Its X-RD diffraction pattern is shown in FIG. 1, and DSC is shown in FIG. 2.

Comparative Example

Preparation of the B-Type Polymorphic Substance of Yonkenafil Hydrochloride

Figure 3:
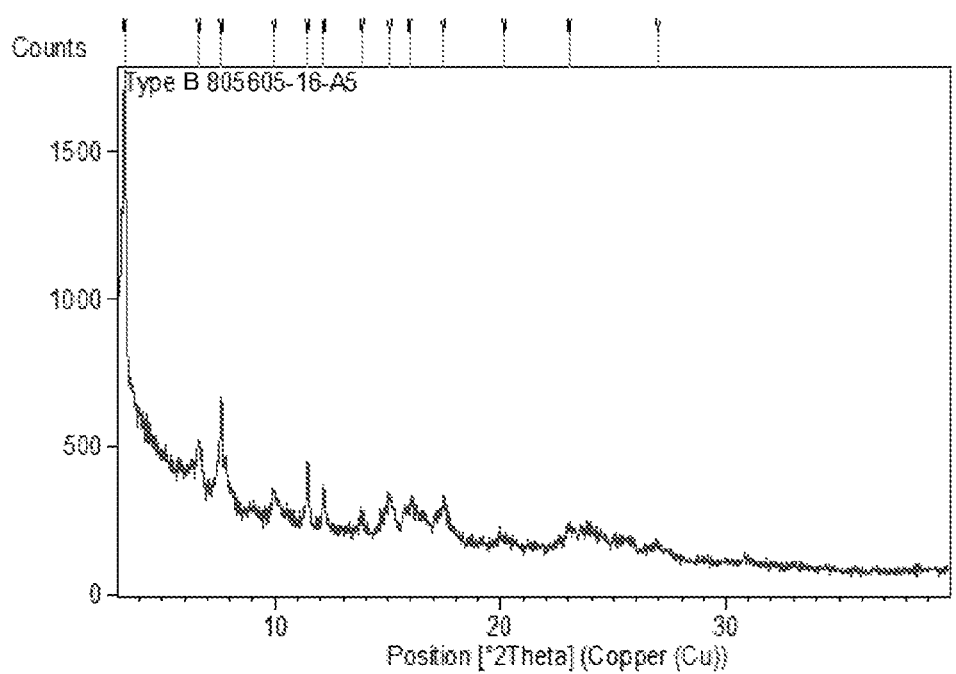
FIG. 3 is an X-RD pattern of the B-type polymorphic substance of yonkenafil hydrochloride.

A free alkali (yonkenafil, prepared according to Chinese Patent Application CN03142399.X, 1.0 g) was dissolved in ethyl ether (10 ml) and dichloromethane (10 ml), and a solution of 4M hydrochloric acid-dioxane (0.51 ml) diluted with ethyl ether (10 ml) was added dropwise thereto under stirring. Upon completion of dropwise addition, the mixture was stirred at room temperature for 20 minutes, filtered, and the resulting solid was dried under reduced pressure to give the B-type polymorphic substance of yonkenafil hydrochloride (1.0 g). Melting Point: 147-150° C., its X-RD diffraction pattern was shown in FIG. 3.

The inventor of the present application accidentally found that the B-type polymorphic substance of yonkenafil hydrochloride can be converted into the A-type polymorphic substance of yonkenafil hydrochloride after standing at the condition of room temperature for one week, indicating that the A-type polymorphic substance of yonkenafil hydrochloride is more stable than the B-type polymorphic substance of yonkenafil hydrochloride.

While the embodiments disclosed in the present invention are as the above, the described content is only the embodiments for facilitating the understanding of the present invention, instead of limiting the present invention. Anyone skilled in the art, under the premise of not deviating from the spirit and scope of the disclosure of the present invention, may make various modifications and variations in the form and details of implementation, for example, the slowly cooling process mentioned in Examples 2-3 may be cooled at a rate in the range of 0.1° C./min to 2.0° C./min, optionally at a rate in the range of 0.1° C./min to 0.8° C./min. For the control of the cooling rate, according to the need of the reaction process, multiple adjustments may be made to obtain the A-type polymorphic substance of yonkenafil hydrochloride.

The patent protection scope of the present invention should still be based on the scope defined by the appended claims.

INDUSTRIAL APPLICABILITY

An A-type polymorphic substance of yonkenafil hydrochloride of the present invention has excellent physical and chemical stability and is easy to be industrially produced, as a pharmaceutically acceptable, stable, novel crystalline form of yonkenafil hydrochloride.

What we claim is:

1. An A-type polymorphic substance of yonkenafil hydrochloride, wherein the X-ray powder diffraction pattern of the polymorphic substance comprises diffraction peaks at three or more 2θ values selected from 8.4°±0.2°, 11.3°±0.2°, 13.9°±0.2°, 14.2°±0.2°, 14.7°±0.2°, 16.8°±0.2°, 17.1°±0.2°, 19.7°±0.2°, 21.0°±0.2°, 21.7°±0.2°, 22.4°±0.2°, 23.3°±0.2°, 23.8°±0.2°, 26.8°±0.2°, 27.5°±0.2°, and 28.0°±0.2°, wherein the 2θ values are obtained by using copper K-alpha radiation.

2. The polymorphic substance of claim 1, wherein cell parameters of the polymorphic substance are substantially as follows:
   cell dimension: a (Å) is equal to 19.1±0.1,
   b (Å) is equal to 12.7±0.1,
   c (Å) is equal to 11.3±0.1,
   volume is equal to 2741±30 Å$^3$,
   space group is P2$_1$/c, and
   density is 1.31±0.01 g/cm$^3$.

3. The polymorphic substance of claim 1, wherein the X-ray powder diffraction pattern of the polymorphic substance comprises diffraction peaks at 2θ values selected from 8.4°±0.2°, 11.3°±0.2°, 13.9°±0.2°, 14.2°±0.2°, 14.7°±0.2°, 16.8°±0.2°, 17.1°±0.2°, 19.7°±0.2°, 21.0°±0.2°, 21.7°±0.2°, 22.4°±0.2°, 23.3°±0.2°, 23.8°±0.2°, 26.8°±0.2°, 27.5°±0.2°, and 28.0°±0.2°, wherein the 2θ values are obtained by using copper K-alpha radiation.

4. The polymorphic substance of claim 3, wherein the X-ray powder diffraction pattern of the polymorphic substance is substantially consistent with that shown in FIG. 1.

5. The polymorphic substance of claim 1, wherein the analysis pattern of the differential scanning calorimetry of the polymorphic substance has endothermic peaks at 34-133° C. and 231-250° C., respectively.

6. The polymorphic substance of claim 5, wherein the analysis pattern of the differential scanning calorimetry of the polymorphic substance is substantially consistent with that shown in FIG. 2.

7. A preparation method for an A-type polymorphic substance of yonkenafil hydrochloride, comprising:
   suspending yonkenafil hydrochloride in an aqueous solution or an organic solvent/water solution, heating to dissolve the yonkenafil hydrochloride, slowly cooling and crystallizing, filtering to collect solid, and drying, to obtain the A-type polymorphic substance of yonkenafil hydrochloride; or,
   achieving a dissolution equilibrium of yonkenafil hydrochloride in an aqueous solution or an organic solvent/water solution, filtering and drying to obtain the A-type polymorphic substance of yonkenafil hydrochloride;
   wherein the organic solvent is a solvent capable of dissolving yonkenafil hydrochloride and miscible with water under the heating conditions.

8. The preparation method of claim 7, wherein the organic solvent is selected from one or more of ethanol, methanol, n-propanol, acetonitrile, isopropanol, acetone, dimethylsulfoxide, N-methylpyrrolidone, or tetrahydrofuran.

9. The preparation method of claim 7, wherein the volume ratio of the organic solvent to water is 99:1-0:100.

10. The preparation method of claim 7, wherein the heating temperature is in the range of 40° C.~100° C.

11. The preparation method of claim 7, wherein the rate of the slowly cooling is in the range of 0.1° C./min~2.0° C./min.

12. An A-type polymorphic substance of yonkenafil hydrochloride prepared by the preparation method of claim 7.

13. A pharmaceutical composition comprising an A-type polymorphic substance of yonkenafil hydrochloride of claim 1.

14. The pharmaceutical composition of claim 13, wherein the pharmaceutical composition is formulated as a solid oral formulation, or as a liquid oral formulation.

15. The pharmaceutical composition of claim 13, further comprising an excipient.

16. A method of using the A-type polymorphic substance of yonkenafil hydrochloride of claim 1 for treating male animal erectile dysfunction, the method comprising administering the A-type polymorphic substance of yonkenafil hydrochloride to the male animal in need, wherein the male animal includes a human.

17. An A-type polymorphic substance of yonkenafil hydrochloride prepared by the preparation method of claim 8.

18. An A-type polymorphic substance of yonkenafil hydrochloride prepared by the preparation method of claim 9.

19. An A-type polymorphic substance of yonkenafil hydrochloride prepared by the preparation method of claim 10.

20. An A-type polymorphic substance of yonkenafil hydrochloride prepared by the preparation method of claim 11.

21. A pharmaceutical composition comprising an A-type polymorphic substance of yonkenafil hydrochloride of claim 2.

22. A pharmaceutical composition comprising an A-type polymorphic substance of yonkenafil hydrochloride of claim 3.

23. A pharmaceutical composition comprising an A-type polymorphic substance of yonkenafil hydrochloride of claim 4.

24. A pharmaceutical composition comprising an A-type polymorphic substance of yonkenafil hydrochloride of claim 5.

25. A pharmaceutical composition comprising an A-type polymorphic substance of yonkenafil hydrochloride of claim 6.

26. A pharmaceutical composition comprising an A-type polymorphic substance of yonkenafil hydrochloride of claim 12.

27. The pharmaceutical composition of claim 14, further comprising an excipient.

28. A method of using the A-type polymorphic substance of yonkenafil hydrochloride of claim 2 for treating male animal erectile dysfunction, the method comprising administering the A-type polymorphic substance of yonkenafil hydrochloride to the male animal in need, wherein the male animal includes a human.

29. A method of using the A-type polymorphic substance of yonkenafil hydrochloride of claim 3 for treating male animal erectile dysfunction, the method comprising administering the A-type polymorphic substance of yonkenafil hydrochloride to the male animal in need, wherein the male animal includes a human.

30. A method of using the A-type polymorphic substance of yonkenafil hydrochloride of claim 4 for treating male animal erectile dysfunction, the method comprising administering the A-type polymorphic substance of yonkenafil hydrochloride to the male animal in need, wherein the male animal includes a human.

31. A method of using the A-type polymorphic substance of yonkenafil hydrochloride of claim 5 for treating male animal erectile dysfunction, the method comprising administering the A-type polymorphic substance of yonkenafil hydrochloride to the male animal in need, wherein the male animal includes a human.

32. A method of using the A-type polymorphic substance of yonkenafil hydrochloride of claim 6 for treating male animal erectile dysfunction, the method comprising administering the A-type polymorphic substance of yonkenafil hydrochloride to the male animal in need, wherein the male animal includes a human.

33. A method of using the A-type polymorphic substance of yonkenafil hydrochloride prepared by the preparation method of claim 7 for treating male animal erectile dysfunction, the method comprising administering the A-type polymorphic substance of yonkenafil hydrochloride to the male animal in need, wherein the male animal includes a human.

34. A method of using the A-type polymorphic substance of yonkenafil hydrochloride prepared by the preparation method of claim 8 for treating male animal erectile dysfunction, the method comprising administering the A-type polymorphic substance of yonkenafil hydrochloride to the male animal in need, wherein the male animal includes a human.

35. A method of using the A-type polymorphic substance of yonkenafil hydrochloride prepared by the preparation method of claim 9 for treating male animal erectile dysfunction, the method comprises administering the A-type polymorphic substance of yonkenafil hydrochloride to the male animal in need, wherein the male animal includes human.

36. A method of using the A-type polymorphic substance of yonkenafil hydrochloride prepared by the preparation method of claim 10 for treating male animal erectile dysfunction, the method comprising administering the A-type polymorphic substance of yonkenafil hydrochloride to the male animal in need, wherein the male animal includes a human.

37. A method of using the A-type polymorphic substance of yonkenafil hydrochloride prepared by the preparation method of claim 11 for treating male animal erectile dysfunction, the method comprising administering the A-type polymorphic substance of yonkenafil hydrochloride to the male animal in need, wherein the male animal includes a human.

38. A method of using the pharmaceutical composition of claim 13 for treating male animal erectile dysfunction and diseases associated with phosphodiesterase 5, the method comprising administering the pharmaceutical composition to the male animal in need, wherein the male animal includes a human.

39. A method of using the pharmaceutical composition of claim 14 for treating male animal erectile dysfunction, the method comprising administering the pharmaceutical composition to the male animal in need, wherein the male animal includes a human.

40. A method of using the pharmaceutical composition of claim 15 for treating male animal erectile dysfunction, the method comprising administering the pharmaceutical composition to the male animal in need, wherein the male animal includes a human.

41. The polymorphic substance of claim 1, wherein the analysis pattern of the differential scanning calorimetry of the polymorphic substance has endothermic peaks at 86.4° C. and 237.9° C., respectively.

42. The preparation method of claim 7, wherein the volume ratio of the organic solvent to water is 98:2-40:60.

43. The preparation method of claim 7, wherein the heating temperature is in the range of 60° C.~90° C.

44. The preparation method of claim 7, wherein the rate of the slowly cooling is in the range of 0.1° C./min~0.8° C./min.

45. The pharmaceutical composition of claim 14, wherein the solid oral formulation is a tablet, a pill, a capsule or a powder; and the liquid oral formulation is a suspension, a solution, an emulsion or a syrup.

46. The pharmaceutical composition of claim 15, wherein the excipient is a functional excipient.

47. A method of using the A-type polymorphic substance of yonkenafil hydrochloride of claim 1 for treating diseases associated with phosphodiesterase 5, the method comprising administering the A-type polymorphic substance of yonkenafil hydrochloride to a subject in need, wherein said diseases associated with phosphodiesterase 5 are male sexual dysfunction, female sexual dysfunction, premature labor, dysmenorrhea, benign prostatic hyperplasia, bladder obstruction, incontinence, regular or irregular angina, hypertension, pulmonary hypertension, congestive heart failure, arteriosclerosis, stroke, peripheral circulatory system diseases, openness reduction of blood vessels, chronic asthma, allergic asthma, bronchitis, allergic rhinitis, glaucoma, gastrointestinal disorders, convulsion precursors, Kawasaki syndrome, nitrate tolerance, multiple sclerosis, diabetic peripheral neurological syndrome, Alzheimer's disease, acute respiratory failure, psoriasis, skin gangrene, cancer cell metastasis, hair loss, nutcracker esophagus, anal fissure or hypoxic vasoconstriction.

48. The method of claim 47, wherein the male sexual dysfunction is male human erectile dysfunction.

49. The pharmaceutical composition of claim 27, wherein the excipient is a functional excipient.

50. A method of using the A-type polymorphic substance of yonkenafil hydrochloride of claim 2 for treating diseases associated with phosphodiesterase 5, the method comprising administering the A-type polymorphic substance of yonkenafil hydrochloride to a subject in need, wherein said diseases associated with phosphodiesterase 5 are male sexual dysfunction, female sexual dysfunction, premature labor, dysmenorrhea, benign prostatic hyperplasia, bladder obstruction, incontinence, regular or irregular angina, hypertension, pulmonary hypertension, congestive heart failure, arteriosclerosis, stroke, peripheral circulatory system diseases, openness reduction of blood vessels, chronic asthma, allergic asthma, bronchitis, allergic rhinitis, glaucoma, gastrointestinal disorders, convulsion precursors, Kawasaki syndrome, nitrate tolerance, multiple sclerosis, diabetic peripheral neurological syndrome, Alzheimer's disease, acute respiratory failure, psoriasis, skin gangrene, cancer cell metastasis, hair loss, nutcracker esophagus, anal fissure or hypoxic vasoconstriction.

51. The method of claim 50, wherein the male sexual dysfunction is male human erectile dysfunction.

52. A method of using the A-type polymorphic substance of yonkenafil hydrochloride of claim 3 for treating diseases associated with phosphodiesterase 5, the method comprising administering the A-type polymorphic substance of yonkenafil hydrochloride to a subject in need, wherein said diseases associated with phosphodiesterase 5 are male sexual dysfunction, female sexual dysfunction, premature labor, dysmenorrhea, benign prostatic hyperplasia, bladder obstruction, incontinence, regular or irregular angina, hypertension, pulmonary hypertension, congestive heart failure, arteriosclerosis, stroke, peripheral circulatory system diseases, openness reduction of blood vessels, chronic asthma, allergic asthma, bronchitis, allergic rhinitis, glaucoma, gastrointestinal disorders, convulsion precursors, Kawasaki syndrome, nitrate tolerance, multiple sclerosis, diabetic peripheral neurological syndrome, Alzheimer's disease, acute respiratory failure, psoriasis, skin gangrene, cancer cell metastasis, hair loss, nutcracker esophagus, anal fissure or hypoxic vasoconstriction.

53. The method of claim 52, wherein the male sexual dysfunction is male human erectile dysfunction.

54. A method of using the A-type polymorphic substance of yonkenafil hydrochloride of claim 4 for treating diseases associated with phosphodiesterase 5, the method comprising administering the A-type polymorphic substance of yonkenafil hydrochloride to a subject in need, wherein said diseases associated with phosphodiesterase 5 are male sexual dysfunction, female sexual dysfunction, premature labor, dysmenorrhea, benign prostatic hyperplasia, bladder obstruction, incontinence, regular or irregular angina, hypertension, pulmonary hypertension, congestive heart failure, arteriosclerosis, stroke, peripheral circulatory system diseases, openness reduction of blood vessels, chronic asthma, allergic asthma, bronchitis, allergic rhinitis, glaucoma, gastrointestinal disorders, convulsion precursors, Kawasaki syndrome, nitrate tolerance, multiple sclerosis, diabetic peripheral neurological syndrome, Alzheimer's disease, acute respiratory failure, psoriasis, skin gangrene, cancer cell metastasis, hair loss, nutcracker esophagus, anal fissure or hypoxic vasoconstriction.

55. The method of claim 54, wherein the male sexual dysfunction is male human erectile dysfunction.

56. A method of using the A-type polymorphic substance of yonkenafil hydrochloride of claim 5 for treating diseases associated with phosphodiesterase 5, the method comprising administering the A-type polymorphic substance of yonkenafil hydrochloride to a subject in need, wherein said diseases associated with phosphodiesterase 5 are male sexual dysfunction, female sexual dysfunction, premature labor, dysmenorrhea, benign prostatic hyperplasia, bladder obstruction, incontinence, regular or irregular angina, hypertension, pulmonary hypertension, congestive heart failure, arteriosclerosis, stroke, peripheral circulatory system diseases, openness reduction of blood vessels, chronic asthma, allergic asthma, bronchitis, allergic rhinitis, glaucoma, gastrointestinal disorders, convulsion precursors, Kawasaki syndrome, nitrate tolerance, multiple sclerosis, diabetic peripheral neurological syndrome, Alzheimer's disease, acute respiratory failure, psoriasis, skin gangrene, cancer cell metastasis, hair loss, nutcracker esophagus, anal fissure or hypoxic vasoconstriction.

57. The method of claim 56, wherein the male sexual dysfunction is male human erectile dysfunction.

58. A method of using the A-type polymorphic substance of yonkenafil hydrochloride of claim 6 for treating diseases associated with phosphodiesterase 5, the method comprising administering the A-type polymorphic substance of yonkenafil hydrochloride to a subject in need, wherein said diseases associated with phosphodiesterase 5 are male sexual dysfunction, female sexual dysfunction, premature labor, dysmenorrhea, benign prostatic hyperplasia, bladder obstruction, incontinence, regular or irregular angina, hypertension, pulmonary hypertension, congestive heart failure, arteriosclerosis, stroke, peripheral circulatory system diseases, openness reduction of blood vessels, chronic asthma, allergic asthma, bronchitis, allergic rhinitis, glaucoma, gastrointestinal disorders, convulsion precursors, Kawasaki syndrome, nitrate tolerance, multiple sclerosis, diabetic peripheral neurological syndrome, Alzheimer's disease, acute respiratory failure, psoriasis, skin gangrene, cancer cell metastasis, hair loss, nutcracker esophagus, anal fissure or hypoxic vasoconstriction.

59. The method of claim 58, wherein the male sexual dysfunction is male human erectile dysfunction.

60. A method of using the A-type polymorphic substance of yonkenafil hydrochloride prepared by the preparation method of claim 7 for treating diseases associated with phosphodiesterase 5, the method comprising administering the A-type polymorphic substance of yonkenafil hydrochloride to a subject in need, wherein said diseases associated with phosphodiesterase 5 are male sexual dysfunction, female sexual dysfunction, premature labor, dysmenorrhea, benign prostatic hyperplasia, bladder obstruction, incontinence, regular or irregular angina, hypertension, pulmonary hypertension, congestive heart failure, arteriosclerosis, stroke, peripheral circulatory system diseases, openness reduction of blood vessels, chronic asthma, allergic asthma, bronchitis, allergic rhinitis, glaucoma, gastrointestinal disorders, convulsion precursors, Kawasaki syndrome, nitrate tolerance, multiple sclerosis, diabetic peripheral neurological syndrome, Alzheimer's disease, acute respiratory failure, psoriasis, skin gangrene, cancer cell metastasis, hair loss, nutcracker esophagus, anal fissure or hypoxic vasoconstriction.

61. The method of claim 60, wherein the male sexual dysfunction is male human erectile dysfunction.

62. A method of using the A-type polymorphic substance of yonkenafil hydrochloride prepared by the preparation method of claim 8 for treating diseases associated with phosphodiesterase 5, the method comprising administering the A-type polymorphic substance of yonkenafil hydrochloride to a subject in need, wherein said diseases associated with phosphodiesterase 5 are male sexual dysfunction, female sexual dysfunction, premature labor, dysmenorrhea, benign prostatic hyperplasia, bladder obstruction, incontinence, regular or irregular angina, hypertension, pulmonary hypertension, congestive heart failure, arteriosclerosis, stroke, peripheral circulatory system diseases, openness reduction of blood vessels, chronic asthma, allergic asthma, bronchitis, allergic rhinitis, glaucoma, gastrointestinal disorders, convulsion precursors, Kawasaki syndrome, nitrate tolerance, multiple sclerosis, diabetic peripheral neurological syndrome, Alzheimer's disease, acute respiratory failure, psoriasis, skin gangrene, cancer cell metastasis, hair loss, nutcracker esophagus, anal fissure or hypoxic vasoconstriction.

63. The method of claim 62, wherein the male sexual dysfunction is male human erectile dysfunction.

64. A method of using the A-type polymorphic substance of yonkenafil hydrochloride prepared by the preparation method of claim 9 for treating diseases associated with phosphodiesterase 5, the method comprising administering the A-type polymorphic substance of yonkenafil hydrochloride to a subject in need, wherein said diseases associated with phosphodiesterase 5 are male sexual dysfunction, female sexual dysfunction, premature labor, dysmenorrhea, benign prostatic hyperplasia, bladder obstruction, incontinence, regular or irregular angina, hypertension, pulmonary hypertension, congestive heart failure, arteriosclerosis, stroke, peripheral circulatory system diseases, openness reduction of blood vessels, chronic asthma, allergic asthma, bronchitis, allergic rhinitis, glaucoma, gastrointestinal disorders, convulsion precursors, Kawasaki syndrome, nitrate tolerance, multiple sclerosis, diabetic peripheral neurological syndrome, Alzheimer's disease, acute respiratory failure, psoriasis, skin gangrene, cancer cell metastasis, hair loss, nutcracker esophagus, anal fissure or hypoxic vasoconstriction.

65. The method of claim 64, wherein the male sexual dysfunction is male human erectile dysfunction.

66. A method of using the A-type polymorphic substance of yonkenafil hydrochloride prepared by the preparation method of claim 10 for treating diseases associated with phosphodiesterase 5, the method comprising administering the A-type polymorphic substance of yonkenafil hydrochloride to a subject in need, wherein said diseases associated with phosphodiesterase 5 are male sexual dysfunction, female sexual dysfunction, premature labor, dysmenorrhea, benign prostatic hyperplasia, bladder obstruction, incontinence, regular or irregular angina, hypertension, pulmonary hypertension, congestive heart failure, arteriosclerosis, stroke, peripheral circulatory system diseases, openness reduction of blood vessels, chronic asthma, allergic asthma, bronchitis, allergic rhinitis, glaucoma, gastrointestinal disorders, convulsion precursors, Kawasaki syndrome, nitrate tolerance, multiple sclerosis, diabetic peripheral neurological syndrome, Alzheimer's disease, acute respiratory failure, psoriasis, skin gangrene, cancer cell metastasis, hair loss, nutcracker esophagus, anal fissure or hypoxic vasoconstriction.

67. The method of claim 66, wherein the male sexual dysfunction is male human erectile dysfunction.

68. A method of using the A-type polymorphic substance of yonkenafil hydrochloride prepared by the preparation method of claim 11 for treating diseases associated with phosphodiesterase 5, the method comprising administering the A-type polymorphic substance of yonkenafil hydrochloride to a subject in need, wherein said diseases associated with phosphodiesterase 5 are male sexual dysfunction, female sexual dysfunction, premature labor, dysmenorrhea, benign prostatic hyperplasia, bladder obstruction, incontinence, regular or irregular angina, hypertension, pulmonary hypertension, congestive heart failure, arteriosclerosis, stroke, peripheral circulatory system diseases, openness reduction of blood vessels, chronic asthma, allergic asthma, bronchitis, allergic rhinitis, glaucoma, gastrointestinal disorders, convulsion precursors, Kawasaki syndrome, nitrate tolerance, multiple sclerosis, diabetic peripheral neurological syndrome, Alzheimer's disease, acute respiratory failure, psoriasis, skin gangrene, cancer cell metastasis, hair loss, nutcracker esophagus, anal fissure or hypoxic vasoconstriction.

69. The method of claim 68, wherein the male sexual dysfunction is male erectile dysfunction.

70. A method of using the pharmaceutical composition of claim 13 for treating diseases associated with phosphodiesterase 5, the method comprising administering the pharmaceutical composition to a subject in need, wherein said diseases associated with phosphodiesterase 5 are male sexual dysfunction, female sexual dysfunction, premature labor, dysmenorrhea, benign prostatic hyperplasia, bladder obstruction, incontinence, regular or irregular angina, hypertension, pulmonary hypertension, congestive heart failure, arteriosclerosis, stroke, peripheral circulatory system diseases, openness reduction of blood vessels, chronic asthma, allergic asthma, bronchitis, allergic rhinitis, glaucoma, gastrointestinal disorders, convulsion precursors, Kawasaki syndrome, nitrate tolerance, multiple sclerosis, diabetic peripheral neurological syndrome, Alzheimer's disease, acute respiratory failure, psoriasis, skin gangrene, cancer cell metastasis, hair loss, nutcracker esophagus, anal fissure or hypoxic vasoconstriction.

71. The method of claim 70, wherein the male sexual dysfunction is male human erectile dysfunction.

72. A method of using the pharmaceutical composition of claim 14 for treating diseases associated with phosphodiesterase 5, the method comprising administering the pharmaceutical composition to a subject in need, wherein said diseases associated with phosphodiesterase 5 are male sexual dysfunction, female sexual dysfunction, premature labor, dysmenorrhea, benign prostatic hyperplasia, bladder obstruction, incontinence, regular or irregular angina, hypertension, pulmonary hypertension, congestive heart failure, arteriosclerosis, stroke, peripheral circulatory system diseases, openness reduction of blood vessels, chronic asthma, allergic asthma, bronchitis, allergic rhinitis, glaucoma, gastrointestinal disorders, convulsion precursors, Kawasaki syndrome, nitrate tolerance, multiple sclerosis, diabetic peripheral neurological syndrome, Alzheimer's disease, acute respiratory failure, psoriasis, skin gangrene, cancer cell metastasis, hair loss, nutcracker esophagus, anal fissure or hypoxic vasoconstriction.

73. The method of claim 72, wherein the male sexual dysfunction is male human erectile dysfunction.

74. A method of using the pharmaceutical composition of claim 15 for treating diseases associated with phosphodiesterase 5, the method comprising administering the pharmaceutical composition to a subject in need, wherein said diseases associated with phosphodiesterase 5 are male sexual dysfunction, female sexual dysfunction, premature labor, dysmenorrhea, benign prostatic hyperplasia, bladder obstruction, incontinence, regular or irregular angina, hypertension, pulmonary hypertension, congestive heart failure, arteriosclerosis, stroke, peripheral circulatory system diseases, openness reduction of blood vessels, chronic asthma, allergic asthma, bronchitis, allergic rhinitis, glaucoma, gastrointestinal disorders, convulsion precursors, Kawasaki syndrome, nitrate tolerance, multiple sclerosis, diabetic peripheral neurological syndrome, Alzheimer's disease, acute respiratory failure, psoriasis, skin gangrene, cancer cell metastasis, hair loss, nutcracker esophagus, anal fissure or hypoxic vasoconstriction.

75. The method of claim 74, wherein the male sexual dysfunction is male human erectile dysfunction.

* * * * *

UNITED STATES PATENT AND TRADEMARK OFFICE
CERTIFICATE OF CORRECTION

PATENT NO. : 9,884,870 B2
APPLICATION NO. : 15/535502
DATED : February 6, 2018
INVENTOR(S) : Haibo Zhang et al.

It is certified that error appears in the above-identified patent and that said Letters Patent is hereby corrected as shown below:

In the Specification

Column 5, Line number 67, please delete "(10 g)" and insert --(1.0 g)--.

Column 6, Line number 14, please delete "70° C" and insert --90° C--.

Signed and Sealed this
Fifteenth Day of March, 2022

Drew Hirshfeld
*Performing the Functions and Duties of the
Under Secretary of Commerce for Intellectual Property and
Director of the United States Patent and Trademark Office*